(12) United States Patent
Axelsson (10) Patent No.: US 7,070,573 B2
(45) Date of Patent: Jul. 4, 2006

(54) TRACTION COLLAR

(76) Inventor: Stefan Axelsson, Mäster Samuelsgatan 34, Stockholm (SE) S-111 57

( * ) Notice: Subject to any disclaimer, the term of this patent is extended or adjusted under 35 U.S.C. 154(b) by 285 days.

(21) Appl. No.: 10/416,302

(22) PCT Filed: Nov. 6, 2001

(86) PCT No.: PCT/SE01/02430

§ 371 (c)(1),
(2), (4) Date: May 9, 2003

(87) PCT Pub. No.: WO02/39939

PCT Pub. Date: May 23, 2002

(65) Prior Publication Data

US 2004/0015111 A1    Jan. 22, 2004

(30) Foreign Application Priority Data

Nov. 10, 2000  (SE) .................................... 0004106

(51) Int. Cl.
*A61F 5/00* (2006.01)

(52) U.S. Cl. ................. 602/18; 602/13; 602/32; 602/36; 128/97.1; 128/845

(58) Field of Classification Search .................. 602/13, 602/17, 18, 32, 36, 61, 74; 128/97.1, 845, 128/846, 857, 869, 870, DIG. 19, DIG. 20, 128/DIG. 23
See application file for complete search history.

(56) References Cited

U.S. PATENT DOCUMENTS

| | | | | |
|---|---|---|---|---|
| 3,164,151 A | * | 1/1965 | Vere Nicoll | 602/18 |
| 3,285,244 A | * | 11/1966 | Cottrell | 602/18 |
| 3,343,532 A | * | 9/1967 | Zumaglini | 602/18 |
| 4,543,947 A | | 10/1985 | Blackstone | |
| 5,062,414 A | * | 11/1991 | Grim | 602/19 |
| 5,402,535 A | * | 4/1995 | Green | 2/468 |
| 5,403,266 A | * | 4/1995 | Bragg et al. | 602/5 |
| 5,752,927 A | * | 5/1998 | Rogachevsky | 602/18 |
| 5,823,982 A | * | 10/1998 | Park | 602/36 |
| 5,916,185 A | * | 6/1999 | Chitwood | 602/18 |
| 6,050,965 A | * | 4/2000 | Pillai | 602/18 |
| 6,447,468 B1 | * | 9/2002 | Hankins et al. | 602/18 |
| 6,592,536 B1 | * | 7/2003 | Argenta | 602/17 |
| 2003/0120192 A1 | * | 6/2003 | Chao | 602/36 |

FOREIGN PATENT DOCUMENTS

GB    2 165 762 A    4/1986

OTHER PUBLICATIONS

Merriam-Webster OnLine, "resilient", printed Jun. 10, 2005, 2 pages.*

* cited by examiner

*Primary Examiner*—Henry Bennett
*Assistant Examiner*—Amanda Wieker
(74) *Attorney, Agent, or Firm*—Young & Thompson (57) ABSTRACT

A traction collar includes a body having an axial extension. The body is equipped with inflatable sections and a device for supplying air to the sections or to dispose of air from the sections. The traction collar is manufactured from cellular plastic material, or a material having corresponding properties. Each of the sections has at least one compartment provided in the body and an air cushion is provided in the compartment.

17 Claims, 6 Drawing Sheets

TRACTION COLLAR

TECHNICAL FIELD OF THE INVENTION

The present invention relates to a traction collar, said collar comprising a body having inflatable sections and means for supplying air to said sections and to dispose of air from said sections.

PRIOR ART

From U.S. Pat. No. 5,752,927 an inflatable traction collar is previously known, said collar having a number of compartments, to which air may be supplied or disposed of in a suitable way. The collar is manufactured from a flexible, elastically expandable plastic material, e.g. polyethylene, rubber and/or similar natural or synthetic substances. However, this material may only to a limited degree adapt to the contours of the person that the collar adjoins to, said portions may for instance be the jaw and the area of the transition between the neck and the shoulders.

OBJECTS AND FEATURES OF THE INVENTION

A primary object of the present invention is to present a traction collar of the type defined above, where a body of the traction collar constitutes an extremely ductile material, e.g. foam rubber, that the height of the traction collar is adjustable, as well as that an inclination of the traction collar is possible.

A further object of the present invention is that an active adjustment of the height of the chin is not supposed to take place.

Still an object of the present invention is that according to a preferred embodiment inflatable sections are arranged at least at two levels that are spaced apart from each other.

At least the primary object of the present invention is realised by means of a traction collar of the type defined above, said traction collar being given the features of the enclosed independent claim. Preferred embodiments of the invention are defined in the dependent claims.

BRIEF DESCRIPTION OF THE DRAWINGS

Below preferred embodiments of a traction collar according to the present invention will be described, reference being made to the accompanying drawings, where.

DETAILED DESCRIPTION OF PREFERRED EMBODIMENTS OF THE INVENTION

Figure 1:
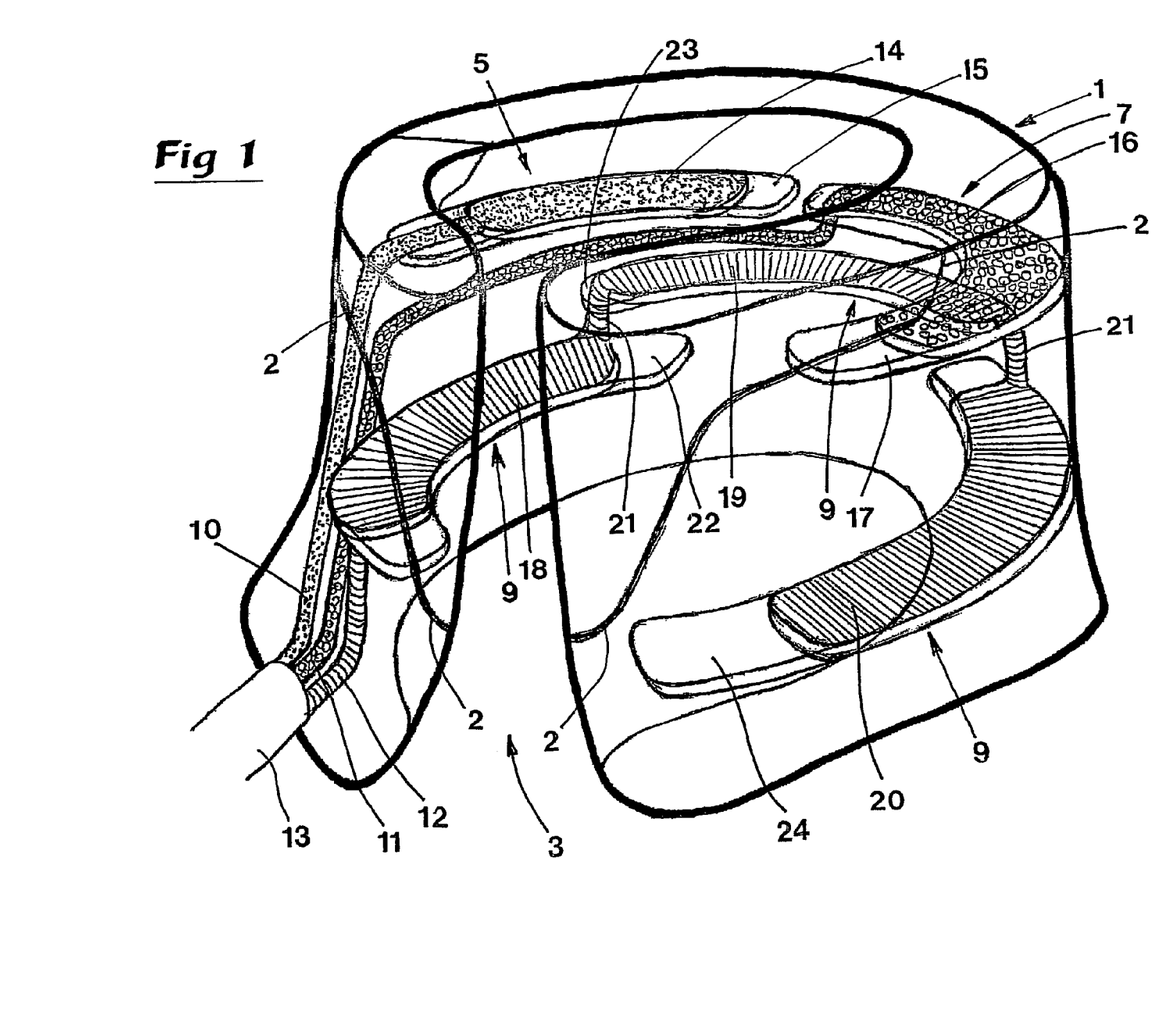
FIG. 1 shows a perspective view of a traction collar according to the present invention, where certain portions of the collar have been made transparent to show the sections arranged in the collar.

The traction collar shown in FIG. 1 comprises a body 1 of cellular plastic, said body 1 possibly being covered, e.g. by means of a cloth or the like. Generally the body 1 is in the shape of a circular cone that is slightly conical, the end of the body 1 that is intended to abut the transition between neck and shoulder of the carrying person having a larger dimension across than the opposite end of the body 1. As is evident from FIG. 1 the body 1 has an axially extending slot 3 that, due to the resilient material of the body 1, may be widened when the traction collar is to be mounted on a carrying person. In the portion of the body 1 that will abut the jaw of the carrying person, i.e. the upper portion in FIG. 1, a softer cellular plastic is used while in the portion of the body 1 that will rest against the lower edge of the skull base and the transition between the neck and the shoulders of the carrying person, i.e. in principle the rest of the body 1 in FIG. 1, a more rigid cellular plastic will be used. The line 2 in FIG. 1 defines the borderline between these two materials.

The traction collar according to the present invention comprises a number of sections. Air may be supplied to these sections or disposed of from these sections. As is evident from FIG. 1 a first section 5 is provided at the top, on the right side of the carrying person, a second section 7 being provided at the top, on the left side of the carrying person and a third section 9 is provided at the bottom, extending substantially around the entire circumference of the body. These sections 5, 7, 9 are separate, i.e. they are completely separated from each other. The first section 5 is adherent to a first conduit 10, the second section 7 is adherent to a second conduit 11 and the third section 9 is adherent to a third conduit 12. Outside the body 1 the conduits 10, 11, 12 are arranged in a common casing in the shape of tube 13 that is connected to a control handle that will be described more in detail below.

The first section 5 comprises on one hand a first inflatable air cushion 14, to which the first conduit 10 is connected. The first section 5 also comprises a first compartment 15 in the body 1, said first air cushion 14 being received in the first compartment 15. The second section 7 comprises on one hand a second inflatable air cushion 16, to which the second conduit 11 is connected. The second section 7 also comprises a second compartment 17 in the body 1, said second air cushion 16 being received in said second compartment 17. The third section 9 comprises on one hand three third inflatable air cushions 18, 19, 20, said third conduit 12 being connected to the air cushion 18. The third air cushions 18, 19, 20 are mutually connected by means of hose shaped connecting portions 21. This means that air may pass through the air cushion 18 to the air cushion 19 and further on through the air cushion 19 to the air cushion 20. The third section 9 also comprises three third compartments 22, 23, 24 in the body 1, said air cushion 18 being received in the compartment 22, the air cushion 19 being received in the compartment 23 and the air cushion 20 being received in the compartment 24. In FIG. 1 air is not supplied to the air cushions 14, 16, 18, 19, 20, i.e. they are in an inactive condition.

The compartments 15, 17, 22, 23, 24, in which air cushions 14, 16, 18, 19, 20 are received, generally are in the shape of slots that define planes essentially perpendicular to the axial direction of the body 1. The planes defined by the compartments 15, 17, 22, 23, 24 are essentially parallel to each other. The first compartment 15 and the second compartment 17 are substantially located in a common plane. As regards the third compartments 22, 23, 24 the two outer compartments 22 and 24 are essentially located in a common plane while the intermediate compartment 23 is located in a plane that is displaced in direction towards the first and second compartments 15 and 17. In the disclosed embodiment the air cushions 14, 16, 18, 19, 20, being in inactive condition and having an extension in the longitudinal direction of the adherent compartments that is smaller than the compartments itself. The reason for this arrangement is that the stress on the material in the body 1 is reduced in connection with activation of the air cushions, i.e. their height is increasing.

Generally, arrangements are taken in order to maintain the air cushions 14, 16, 18, 19, 20 in the adherent compartment 15, 17, 22, 23, 24 also when the air cushions 14, 16, 18, 19, 20 are activated, i.e. when air is supplied. Such an arrangement may be effected in several ways. In exemplifying and non-limiting purpose an adhesive joint between certain portions of the air cushions 14, 16, 18, 19, 20 and the surfaces defining the adherent compartments 15, 17, 22, 23, 24 may be mentioned. In this connection it might be suitable that the portions of the air cushions 14, 16, 18, 19, 20 that are adhered to the surfaces defining the adherent compartments 15, 17, 22, 23, 24 constitute a non-elastic material while the rest of the portions of the air cushions 14, 16, 18, 19, 20 constitute an elastic material.

Figure 2:
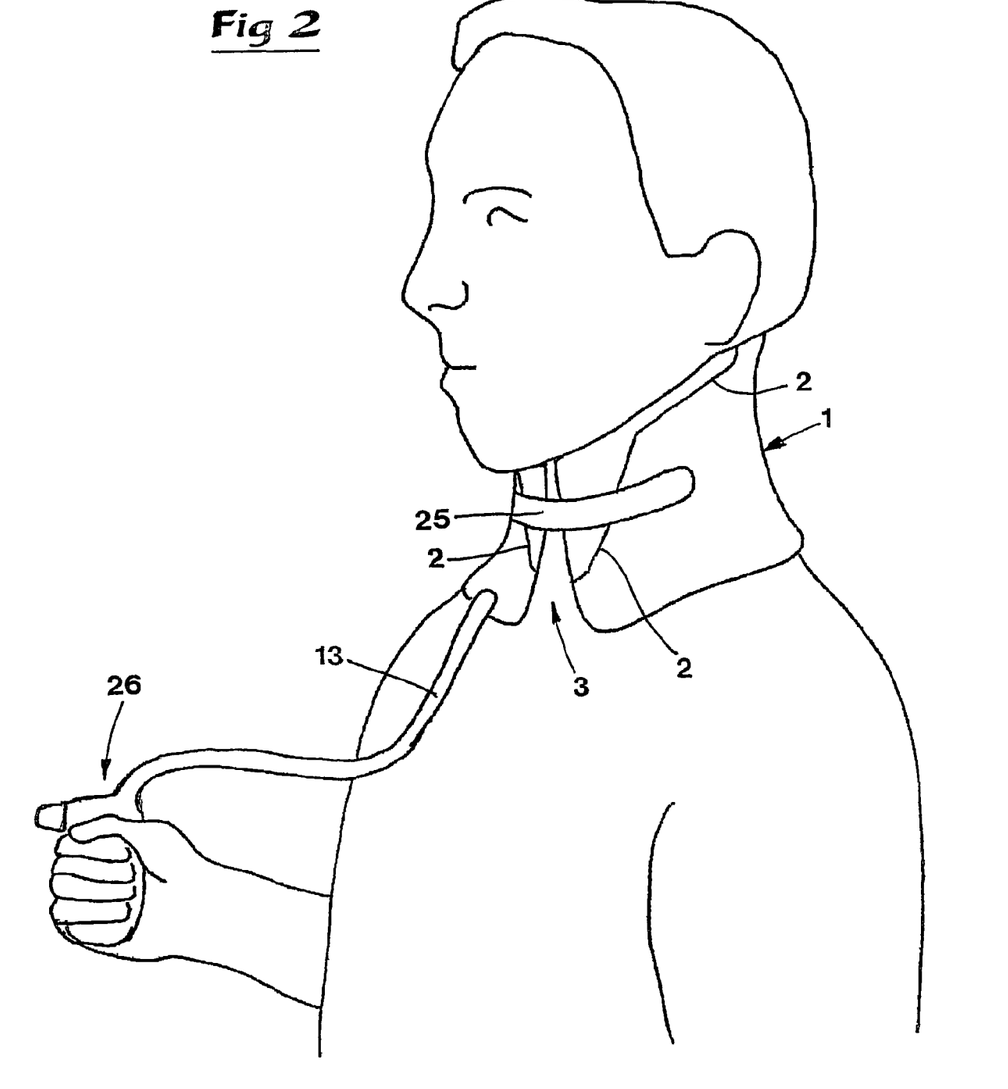
FIG. 2 shows the collar schematically when the collar is mounted on a carrying person.

In FIG. 2 it is schematically shown how the traction collar according to the present invention is mounted on a carrying person. Some portions of the axial end surfaces of the body define supporting surfaces that on one hand abut the rear, lower edge of the skull base of the carrying person and on the other hand abut the transition between the neck and the shoulders of the carrying person. The portions of the body 1 that constitute these supporting surfaces are manufactured from a more rigid cellular plastic. The jaw of the carrying person rests against the portions of the body 1 that constitute a softer cellular plastic. In this connection it should be pointed out that for a certain type of treatment by using a traction collar it happens that the rear portion of the body 1 is lifted. In connection therewith the jaw of the carrying person will be displaced somewhat downwards, this being facilitated due to the fact that the jaw rests against a portion of the body 1 that constitutes a softer cellular plastic.

The edges of the body 1 that define the slot 3 are mutually connected by means of a strap 25 or the like, the end portions of said strap 25 being connected to the body 1. The length of the strap 25 may be varied for adaption to different thickness of the neck of the carrying person. Preferably, the end portions of the strap 25 are connected to the body by means of VELCRO®, hook and loop fastener tape (not shown).

The tube 13, that runs from the body, holds the conduits 10, 11, 12. The end of said tube 13, remote from the body 1, is connected to a control unit 26 that is activated by the carrying person. The control unit is shown more in detail in FIG. 3. As is evident from FIG. 3 the control unit 26 comprises a cover 27, in which a generally cylindrical distribution means 28 is provided for the air that is supplied to the sections 5, 7, 9 or disposed of from the sections 5, 7, 9. In the cover 27 a bellow 29 is also provided and by said bellow 29 air may be supplied to the sections 5, 7, 9, via the distribution means 28.

Figure 3:
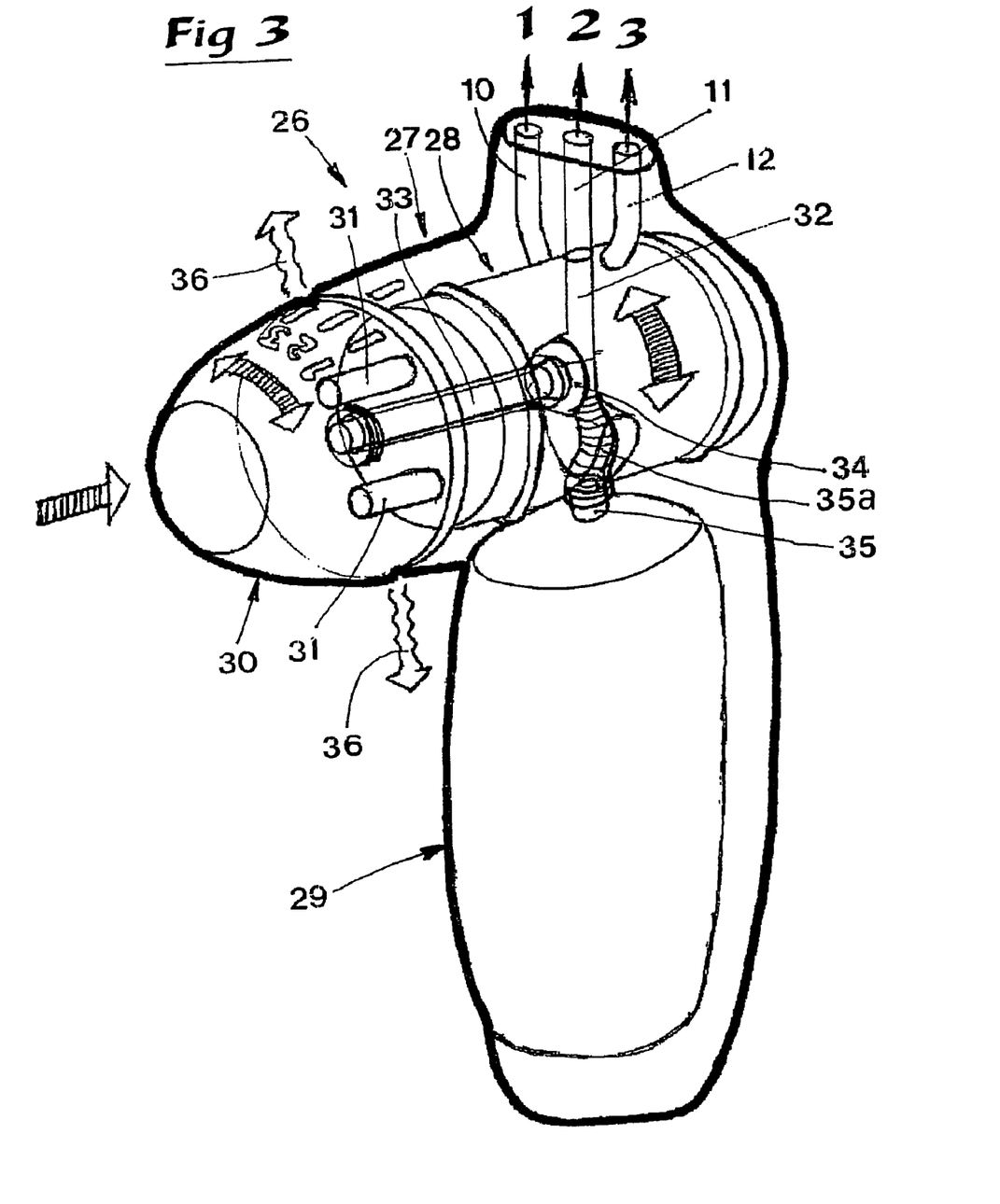
FIG. 3 shows in detail the interior of the control means for supply of air to the sections of the traction collar.

According to the embodiment of the control unit 26, shown in FIG. 3, a portion 30 of the cover 27 is rotatable relative to the rest of the cover 27. This portion 30 is drivingly connected to the distribution means 28, via two pins 31. When the portion 13 is rotated the distribution means 28 will also rotate to a corresponding degree.

From FIG. 3 the schematic design of the distribution means 28 is also evident. A passage 32, for the supply of or disposal of air, extends in radial direction in the cylindrical distribution means 28. The first passage 32 has one end in the area of the radial centre of the distribution means 28 while the other end extends through the envelope surface of the cylindrical distribution means 28. A second passage 33 of the distribution means 28 extends axially in the radial centre of the distribution means 28, said second passage 33 having one end in the area of the end of the first passage 32 that is in the radial centre of the distribution means 28 while the other end of the second passage 33 extends through an end surface of the cylindrical distribution means 28. Through axial displacement of the second passage 33, said second passage 33 may be connected to the first passage 32 via a sealing arrangement 34.

The ends of the conduits 10, 11, 12 that faces away from the body 1 are also fixed in the cover 27, the openings of the conduits 10, 11, 12 being located directly adjacent the cylindrical envelope surface of the control unit 26, more precisely the openings of the conduits 10, 11, 12 being oriented in such a way that the openings always are located directly in front of the opening of the first passage 32. When the rotatable portion 30 of the cover 27 is in the position that is marked by "1" the opening of the conduit 10 is located directly opposite the opening of the first passage 32, when the rotatable portion 30 of the cover 27 is in the position that is marked by "2" the opening of the conduit 11 is located directly opposite the first passage 32 and when the rotatable portion 30 of the cover 27 is in the position marked by "3" the opening of the conduit 12 is located directly opposite the first passage 32.

The bellow 29 of the control unit 26 has a nipple 35 in connection with the distribution means 28 and by the nipple 35 compressed air may be transferred from the bellow 29 to the distribution means 28 via a hose 35a that extends between the nipple 35 and a first passage 32. Then the air is carried further in any of the conduits 10, 11, 12 to the adherent section 5, 7, 9. Which conduit 10, 11, 12 that is chosen is effected by rotation of the rotatable portion 30 in the way that has been described above. In the first passage 32 there is a check valve arrangement (not shown) that guarantees that air supplied to any of the sections 5, 7, 9 is not allowed to flow backwards in the conduits 10, 11, 12.

Air may also be evacuated from any of the sections 5, 7, 9 via the adherent conduit 10, 11, 12. In this case the check valve arrangement is opened in order to make air flow from any of the sections 5, 7, 9, via the first passage 32 and the second passage 33, and then out in the open air. This is symbolised by the arrows 36 in FIG. 3.

Figure 4:
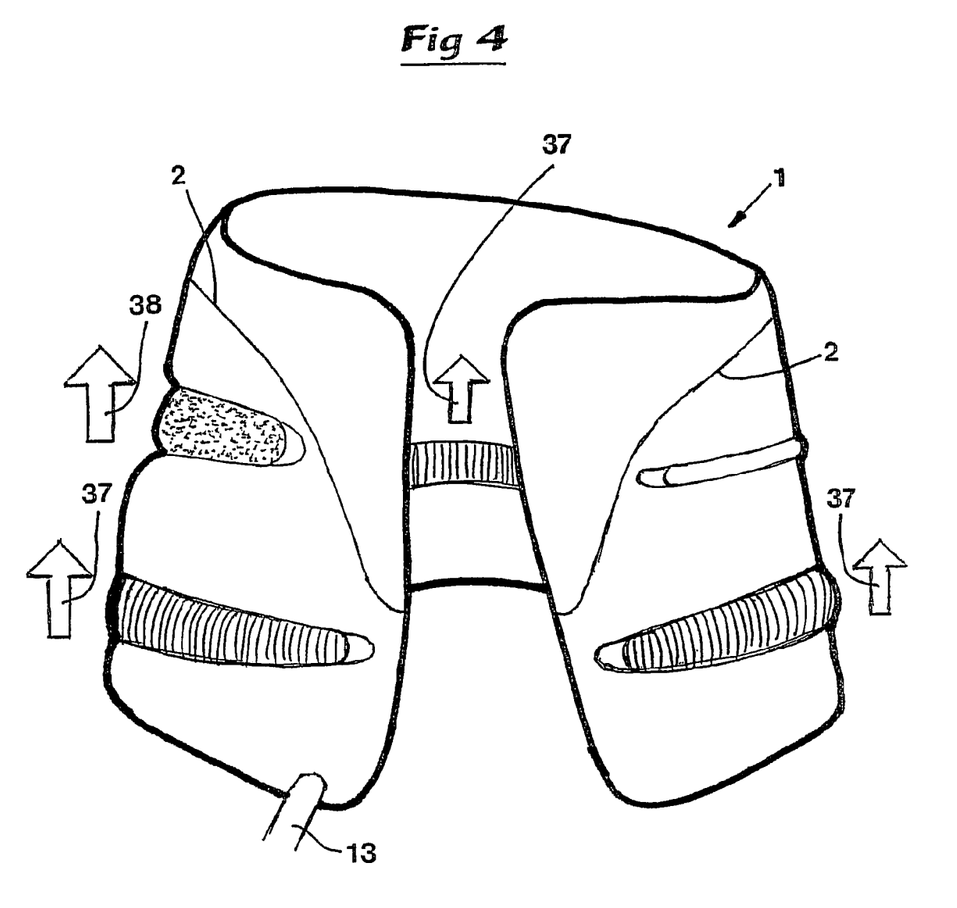
FIG. 4 shows a front view of the traction collar according to the present invention where the lower sections and an upper section on the right side of the carrying person are filled with air.

In FIG. 4 the body 1 is shown schematically when air has been supplied to the first section 5 and the third section 9. By supply of air to the third section 9 a general increase in height is achieved of the body 1 of the traction collar according to the present invention, said generally increase in height being symbolised by the arrows 37. By supply of air to the first section 5 a further increase in height is achieved of the body 1 on the right side of the carrying person (left side in FIG. 4), this further increase in height being symbolised by the arrow 38.

Figure 5:
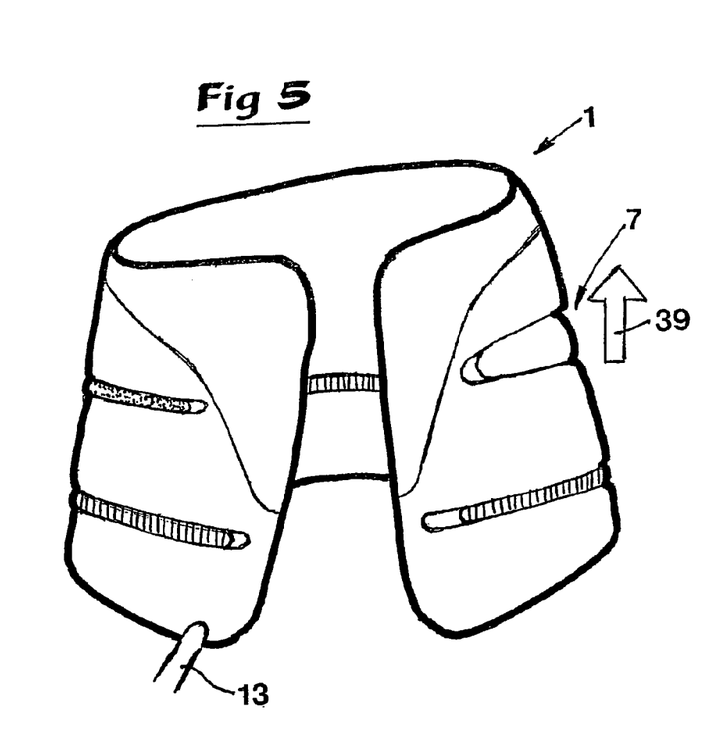
FIG. 5 shows a front view of the traction collar according to the present invention when an upper section on the left side of the carrying person is filled with air.

In FIG. 5 the body 1 is shown schematically when air has been supplied to the second section 7 only. Thereby an increase in height is achieved of the body 1 on the left side of the carrying person (right side in FIG. 5), said increase in height being symbolised by the arrow 39.

Figure 6:
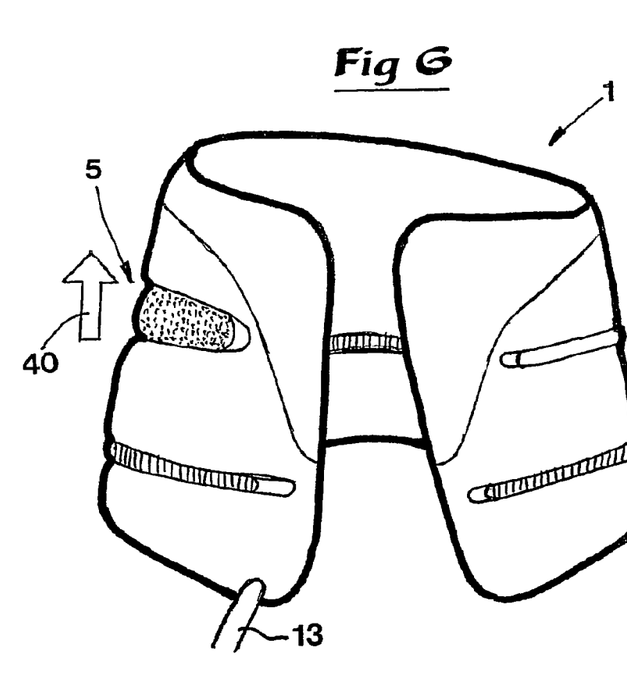
FIG. 6 shows a front view of the traction collar according to the present invention when an upper section on the right side of the carrying person is filled with air.

In FIG. 6 the body 1 is shown schematically when air has been supplied to the first section 5 only. Thereby an increase in the height is achieved of the body 1 on the right side of the carrying person (left side in FIG. 6), said increase in height being symbolised by the arrow 40.

By studying FIGS. 4–6 it is realised that there are a number of alternatives regarding the possibilities to regulate the height expansion of the body 1. This is of extreme important since certain types of neck pains causes obliquity of the neck. In this connection it should also be mentioned that as regards the traction collar according to the present invention there is in principle a possibility to have a continuous adjustment of the height expansion of the body, this being effected by supplying a limited volume air to each section 5, 7, 9.

Figure 7:
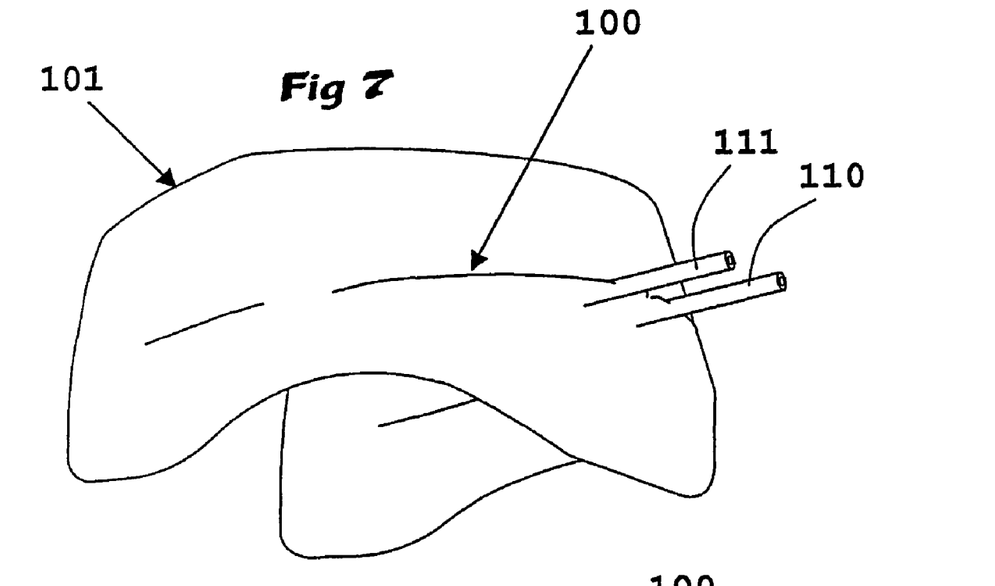
FIG. 7 shows a perspective view, inclined from behind, of an alternative embodiment of a traction collar according to the present invention.
Figure 8:
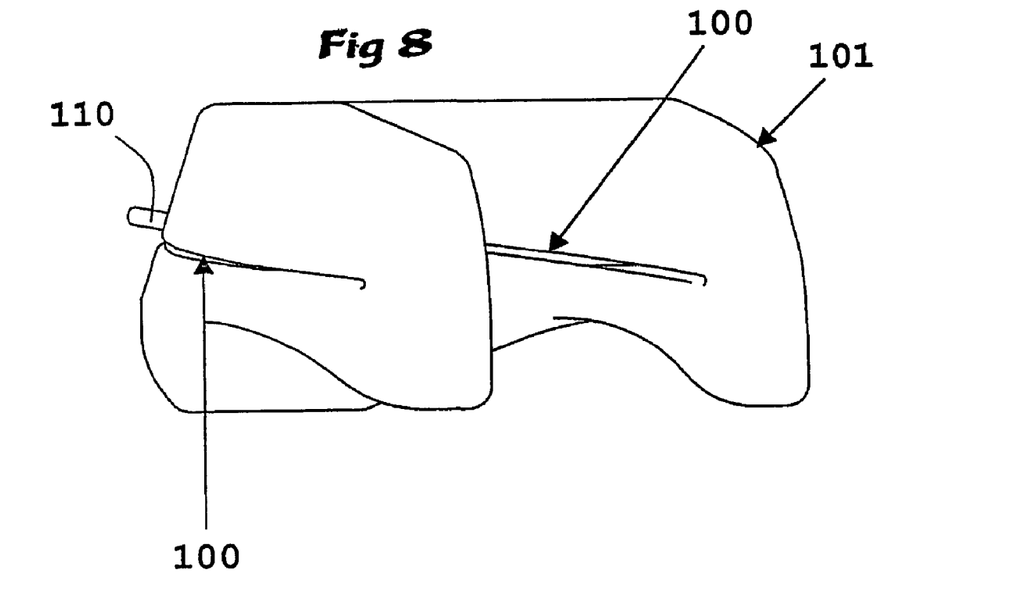
FIG. 8 shows a perspective view, inclined from the front, of the traction collar according to FIG. 7.

In FIGS. 7 and 8 an alternative embodiment of a traction collar according to the present invention is schematically shown, said embodiment comprising sections for air supply at only one level. This is indicated in FIGS. 7 and 8 by a generally radial parting section 100 that separates the traction collar in an upper portion and lower portion. At the level defined by the parting section 100 two separate sections (not shown) are provided, said sections in principle structurally corresponding to the sections 5 and 7 in the embodiment according to FIGS. 1–6. The separation of the sections is indicated by the two conduits 110 and 111 that are drawn in FIGS. 7 and 8. Since the sections are separate the traction collar may be inclined, this being an extremely important feature of the present invention. A general increase in height of the traction collar may also be provided through these sections if an equal amount of air is supplied to each of them.

The body itself 101 is likewise the embodiment according to FIGS. 1–6 manufactured from cellular plastic. Cellular plastic of different properties, e.g. softness, may be used in different portions of the body 101.

Feasible Modifications of the Invention

In the embodiment described above of the body 1 two types of cellular plastic being present, the portion abutting the jaw of the carrying person being softer than the cellular plastic in the rest of the body 1. Alternatively, the entire upper portion of the body 1; 101 may be manufactured from a softer cellular plastic. However, within the scope of the invention it is also feasible that the entire body 1; 101 constitutes the same type of cellular plastic. In this connection it should be pointed out that within the scope of the present invention the body 1; 101 is not necessarily manufactured from cellular plastic but also other resilient plastic materials are feasible.

In the embodiment described above the inflatable sections 5, 7, 9 are arranged at different levels in the direction of height of the body 1. However, within the scope of the invention alternative locations of the sections in height direction of the body 1 are feasible. In exemplifying an non-limiting purpose it may be mentioned that the sections 5 and 7 that primarily effects the inclination of the body 1 may be located at a bottom of the body 1, i.e. closest to the transition between neck and shoulders of the carrying person. It may also be that this section 9 comprises air cushions that are located at one single level in height direction/axial direction of the body 1. In such a case a long continuous slot is created transverse to the axial direction of the body 1. In such a case the body 1 should be surrounded by a cover that on one hand guarantees the stability of the body and on the other hand guarantees that the air cushions are maintained in their adherent compartments.

In the embodiment described above it is stated that the air cushions 14, 16, 18, 19, 20 are maintained in the adherent compartments 15, 17, 22, 23, 24 through adhesion joints. However, within the scope of the present invention a number of alternative solutions are feasible. In exemplifying and non-limiting purposes an arrangement may be mentioned where the body 1 is enclosed in an elastic cover that is connected to the body 1 in conformity to the shape of the body 1. Thereby, it is guaranteed that the air cushions 14, 16, 18, 19, 20 are maintained in the adherent compartments 15, 17, 22, 23, 24.

In order to more evenly distribute and also increase the effect of the height expansion of the air cushions 14, 16, 18, 19, 20 of the traction collar according to the present invention it is also feasible that between the air cushions 14, 16, 18, 19, 20 and the cellular plastic rulers are provided, said rulers having a certain stiffness and if necessary being connected to the air cushions and the cellular plastic in a suitable way.

As regards the control unit 26 described above, said unit 26 may be designed in several different ways. The structural design that has been schematically described above constitutes only an example.

In the embodiment described above the control unit 26 is equipped with a manually activated bellow 29. However, within the scope of the present invention it is also feasible to have other means that generates compressed air. In exemplifying and non-limiting purpose a battery driven motor may be mentioned, this being suitable if the traction collar is to be used by disabled persons.

The invention claimed is:

1. A traction collar comprising:
   a body having at least two slot-shaped compartments and an air cushion received in a respective one of said at least two compartments; and
   means for supplying air to said air cushion or to dispose of air from said air cushion,
   said body being a cellular plastic material, and
   said air cushion extending in a longitudinal direction of said compartments less than a length of said compartments when said air cushion is in an inactive position,
   wherein said at least two slot-shaped compartments are separated from each other, two of said compartments are in planes that are parallel to each other.

2. The traction collar according to claim 1, wherein the body is in the shape of a circular cone having an axially extending slot.

3. The traction collar according to claim 2, wherein each said air cushion has an extension transverse to the axial extension of said body.

4. The traction collar according to claim 2, wherein the body has three slot-shaped compartments that are separated from each other, said two slot-shaped compartments are located at substantially a same level in the axial direction of the body.

5. The traction collar according to claim 2, wherein said body includes two different kinds of resilient plastic material, a softer material is provided in an area of the axial end of the body that is adapted to contacts a jaw of a carrying person, and a more rigid plastic material is provided in the rest of the body.

6. The traction collar according to claim 1, wherein said at least two slot-shaped compartments are perpendicular to an axial direction of said body.

7. The traction collar according to claim 6, wherein the body has three slot-shaped compartments that are separated from each other, said two slot-shaped compartments are located at substantially a same level in the axial direction of the body.

8. The traction collar according to claim 6, wherein the body includes two different kinds of resilient plastic material, a softer material is provided in an area of an axial end of the body that is adapted to contacts a jaw of a carrying person, and a more rigid plastic material is provided in the rest of the body.

9. The traction collar according to claim 1, wherein said body has three slot-shaped compartments that are separated from each other, said two compartments are located at substantially a same level in the axial direction of the body.

10. The traction collar according to claim 1, wherein each air cushion is adherent to a separate conduit in order to supply air to the respective air cushion or dispose of air from the respective air cushion.

11. The traction collar according to claim 10, wherein air is supplied to the air cushion or disposed of from the air cushion by a control unit that comprises a distribution means having air passages that are able to be connected to an arbitrary conduit, said control unit comprises means for generating compressed air.

12. The traction collar according to claim 1, wherein the body includes two different kinds of resilient plastic material, a softer material is provided in the area of the axial end of the body that is adapted to contacts a jaw of a carrying person, and a more rigid plastic material is provided in the rest of the body.

13. A traction collar comprising:
a body having at least one slot-shaped compartment and an air cushion received in a respective one of said at least one compartment; and
means for supplying air to said air cushion or to dispose of air from said air cushion,
said body being a cellular plastic material, and
said air cushion extending in a longitudinal direction of said compartment less than a length of said compartment when said air cushion is in an inactive position,
wherein the body has two air cushions that are separated from each other and located at substantially the same level.

14. A traction collar comprising:
a body having an axial extension, said body having a plurality of slot-shaped compartments, each of said compartments having an air cushion member therein, said air cushion member being spaced apart from end walls of a respective one of said compartments, when said air cushion member is in an inactive position; and
means for supplying air to said air cushion member or to dispose of air from said air cushion member,
wherein the body is manufactured from an elastic plastic material.

15. A traction collar comprising:
a substantially conical, plastic body having an axially extending slot and being divided into plural sections, each of said plural sections having a respective slot-shaped cavity;
an inflatable member within each said respective cavity; and
an inflation/deflation device that inflates/deflates said inflatable member
said inflatable member extending in a longitudinal direction of the cavity, said inflatable member being spaced apart from end walls of said cavity in an inflated position and in a deflated position.

16. The traction collar according to claim 15, wherein each said respective cavity extends transverse to an axial direction of said body.

17. The traction collar according to claim 16, wherein said body is a cellular plastic material.

* * * * *